US008889655B2

(12) United States Patent
London Brown et al.

(10) Patent No.: US 8,889,655 B2
(45) Date of Patent: Nov. 18, 2014

(54) COMPOSITIONS AND METHODS FOR PREVENTING INFECTIOUS DISEASES IN FEMALES

(71) Applicant: Aegis Women's Health Technologies, Raleigh, NC (US)

(72) Inventors: Allison London Brown, Raleigh, NC (US); David Brown Robinson, Schaumburg, IL (US); Shantanu Gaur, Canonsburg, PA (US); Samuel Gideon Levy, Paris (FR); Samuel Mack Hudson, Raleigh, NC (US)

(73) Assignee: Aegis Women's Health Technologies, Raleigh, NC (US)

( * ) Notice: Subject to any disclaimer, the term of this patent is extended or adjusted under 35 U.S.C. 154(b) by 0 days.

(21) Appl. No.: 13/948,127

(22) Filed: Jul. 22, 2013

(65) Prior Publication Data
US 2014/0024615 A1   Jan. 23, 2014

Related U.S. Application Data

(60) Provisional application No. 61/673,769, filed on Jul. 20, 2012, provisional application No. 61/673,773, filed on Jul. 20, 2012.

(51) Int. Cl.
*A61K 31/722* (2006.01)
*A61K 9/00* (2006.01)
*A61K 9/06* (2006.01)
*A61K 9/70* (2006.01)

(52) U.S. Cl.
CPC ............. *A61K 9/0034* (2013.01); *A61K 31/722* (2013.01); *A61K 9/06* (2013.01); *A61K 9/7007* (2013.01)
USPC ......................................................... 514/55

(58) Field of Classification Search
None
See application file for complete search history.

(56) References Cited

U.S. PATENT DOCUMENTS

| | | | |
|---|---|---|---|
| 5,336,208 A | 8/1994 | Rosenbluth et al. | |
| 5,955,502 A | 9/1999 | Hansen et al. | |
| 6,638,296 B2 | 10/2003 | Levinson | |
| 6,890,344 B2 | 5/2005 | Levinson | |
| 2002/0007028 A1 | 1/2002 | Parker et al. | |
| 2008/0081056 A1 | 4/2008 | Nussinovitch et al. | |
| 2009/0226541 A1* | 9/2009 | Scholz et al. | 424/672 |

FOREIGN PATENT DOCUMENTS

| | | |
|---|---|---|
| WO | 9211825 A1 | 7/1992 |
| WO | 9745066 A1 | 12/1997 |
| WO | 0015192 A1 | 3/2000 |
| WO | 0144401 A1 | 6/2001 |
| WO | 02065959 A1 | 8/2002 |
| WO | 03041564 A2 | 5/2003 |
| WO | 2004041313 A2 | 5/2004 |
| WO | 2004093887 A1 | 11/2004 |
| WO | 2005082431 A1 | 9/2005 |
| WO | 2006021054 A1 | 3/2006 |
| WO | 2007096748 A2 | 8/2007 |
| WO | 2007142704 A2 | 12/2007 |
| WO | 2008088911 A2 | 7/2008 |
| WO | 2009028965 A2 | 3/2009 |
| WO | 2009056602 A1 | 5/2009 |
| WO | 2011092653 A2 | 8/2011 |

OTHER PUBLICATIONS

Hurler et al. J. Funct. Biomater. 2012, 3, 37-48, Jan. 6, 2012.*
Kenney, Recurrent Cystitis in Women, internet article, patient.co.uk., Jan. 24, 2012.*
Ikäheimo R, Siitonen A, Heiskanen T, Kärkkäinen U, Kuosmanen P, Lipponen P, Mäkelä PH. Recurrence of urinary tract infection in a primary care setting: analysis of a 1-year follow-up of 179 women. Clin Infect Dis. Jan. 1996;22(1):91-99.
Foxman B, Barlow R, D'Arcy H, Gillespie B, Sobel JD. Urinary tract infection: self-reported incidence and associated costs. Ann Epidemiol. Nov. 2000;10(8):509-515.
Aka-Any-Grah A, Bouchemal K, Koffi A, Agnely F, Zhang M, Djabourov M, Ponchel G. Formulation of mucoadhesive vaginal hydrogels insensitive to dilution with vaginal fluids. Eur J Pharm Biopharm. Oct. 2010;76(2):296-303.
Andrews GP, Donnelly L, Jones DS, Curran RM, Morrow RJ, Woolfson AD, Malcolm RK. Characterization of the rheological, mucoadhesive, and drug release properties of highly structured gel platforms for intravaginal drug delivery. Biomacromolecules. Sep. 14, 2009:10(9):2427-2435.
Baloglu E, Ay Senyigit Z, Karavana SY, Vetter A, Metin DY, Hilmioglu Polat S, Guneri T, Bernkop-Schnurch A. In vitro evaluation of mucoadhesive vaginal tablets of antifungal drugs prepared with thiolated polymer and development of a new dissolution technique for vaginal formulations. Chem Pharm Bull (Tokyo). 2011:59(8):952-958.
Beerepoot MA, ter Riet G, Nys S, van der Wal WM, de Borgie CA, de Reijke TM, Prins JM, Koeijers J, Verbon A, Stobberingh E, Geerlings SE. *Lactobacilli* vs antibiotics to prevent urinary tract infections: a randomized, double-blind, noninferiority trial in postmenopausal women. Arch Intern Med. May 14, 2012;172(9):704-712.
Bernkop-Schnürch A, Dünnhaupt S. Chitosan-based drug delivery systems. Eur J Pharm Biopharm. Aug. 2012;81(3):463-469.
Bonferoni MC, Giunchedi P, Scalia S, Rossi S, Sandri G, Caramella C. Chitosan gels for the vaginal delivery of lactic acid: relevance of formulation parameters to mucoadhesion and release mechanisms. AAPS PharmSciTech. 2006;7(4):104.

(Continued)

*Primary Examiner* — Layla Bland
(74) *Attorney, Agent, or Firm* — Nifong, Kiefer & Klinck PLLC

(57) ABSTRACT

A product that includes a bioadhesive treatment solution for prevention of infectious diseases in the urinary tract of a female is provided. The product includes a polysaccharide. The product is positioned over the urinary tract of a female to act as a barrier against infectious transfer. A method for applying the product and a method for making the product are also disclosed.

15 Claims, 9 Drawing Sheets

(56) References Cited

OTHER PUBLICATIONS

Brubaker L, Harris T, Gleason D, Newman D, North B. The external urethral barrier for stress incontinence: a multicenter trial of safety and efficacy. Miniguard Investigators Group. Obstet Gynecol. Jun. 1999;93(6):932-937.
Mizrahi B, Golenser J, Wolnerman JS, Domb AJ. Adhesive tablet effective for treating canker sores in humans. J Pharm Sci. Dec. 2004;93(12):2927-2935.
Chang Y, Yandi W, Chen WY, Shih YJ, Yang CC, Chang Y, Ling QD, Higuchi A. Tunable bioadhesive copolymer hydrogels of thermoresponsive poly(N-isopropyl acrylamide) containing zwitterionic polysulfobetaine. Biomacromolecules. Apr. 12, 2010;11(4)1101-1110.
Stapleton AE, Au-Yeung M, Hooton TM, Fredricks DN, Roberts PL, Czaja CA, Yarova-Yarovaya Y, Fiedler T, Cox M, Stamm WE. Randomized, placebo-controlled phase 2 trial of a *Lactobacillus crispatus* probiotic given intravaginally for prevention of recurrent urinary tract infection. Clin Infect Dis. May 2011;52(10):1212-1217.
Francisco Cruz, Miriam Dambros, Kurt G. Naber, Hartwig W. Bauer, Gabriel Cozma. Recurrent Urinary Tract Infections: Uro-VaxomW, a New Alternative. European Urology Supplements, Sep. 2009, vol. 8, Issue 9, 762-768.
Curran RM, Donnelly L, Morrow RJ, Fraser C, Andrews G, Cranage M, Malcolm RK, Shattock RJ, Woolfson AD. Vaginal delivery of the recombinant HIV-1 clade-C trimeric gp140 envelope protein CN54gp140 within novel rheologically structured vehicles elicits specific immune responses. Vaccine. Nov. 12, 2009;27(48):6791-6798.
Donnelly L, Curran RM, Tregoning JS, McKay PF, Cole T, Morrow RJ, Kett VL, Andrews GP, Woolfson AD, Malcolm RK, Shattock RJ. Intravaginal immunization using the recombinant HIV-1 clade-C trimeric envelope glycoprotein CN54gp140 formulated within lyophilized solid dosage forms. Vaccine. Jun. 15, 2011;29(27):4512-4520.
Dominique Duchene, Gilles Ponchel. Bioadhesion of solid oral dosage forms, why and how? European Journal of Pharmaceutics and Biopharmaceutics, Jul. 1997;44(1):15-23.
Female sexual pain disorders, Evaluation and management. 1st edition. Edited by Andrew. T. Goldstein, Caroline F. Pukall and Irwin Goldstein. 2008 Blackwell Publishing Limited. ISBN: 978-1-405-18398-7.
Forbes CJ, Lowry D, Geer L, Veazey RS, Shattock RJ, Klasse PJ, Mitchnick M, Goldman L, Doyle LA, Muldoon BC, Woolfson AD, Moore JP, Malcolm RK. Non-aqueous silicone elastomer gels as a vaginal microbicide delivery system for the HIV-1 entry inhibitor maraviroc. J Control Release. Dec. 10, 2011;156(2):161-169.
Francois M, Snoeckx E, Putteman P, Wouters F, De Proost E, Delaet U, Peeters J, Brewster ME. A mucoadhesive, cyclodextrin-based vaginal cream formulation of itraconazole. AAPS PharmSci. 2003;5(1):E5.
Trautner, B. W., Gupta, K. The Advantages of Second Best Preventing Recurrent Cystitis While Sparing the Microbiome. Arch Intern Med., May 14, 2012;172(9):712-714.
Hellebrekers BW, Trimbos-Kemper GC, van Blitterswijk CA, Bakkum EA, Trimbos JB. Effects of five different barrier materials on postsurgical adhesion formation in the rat. Hum Reprod. Jun. 2000;15(6):1358-1363.
Hills BA. Surface-active phospholipid: a Pandora's box of clinical applications. Part II. Barrier and lubricating properties. Intern Med J. May-Jun. 2002;32(5-6):242-2451.
Hooton TM. Clinical practice. Uncomplicated urinary tract infection. N Engl J Med. Mar. 15, 2012;366(11):1028-1037.
Kuen Yong Lee and David J. Mooney. Hydrogels for Tissue Engineering. Chemical reviews Jul. 2001;101(7):1869-1879.
Antonella Agodi and Martina Barchitta Epidemiology and Control of Urinary Tract Infections in Intensive Care Patients, Clinical Management of Complicated Urinary Tract Infection. (2011). Edited by Dr. Ahmad Nikibakhsh.
Andrews GP, Laverty TP, Jones DS. Mucoadhesive polymeric platforms for controlled drug delivery. Eur J Pharm Biopharm. Mar. 2009;71(3):505-518.

Kiser PF, Mahalingam A, Fabian J, Smith E, Damian FR, Peters JJ, Katz DF, Elgendy H, Clark MR, Friend DR. Design of tenofovir-UC781 combination microbicide vaginal gels. J Pharm Sci. May 2012;101(5):1852-1864.
J.S. Krautha,*, H. Rasoamiaramananaa, H. Barlettab, P.Y. Barrierc, M. Grisard-Anafd, J. Lienharte, J. Mermetf, R. Vautherine, J.L. Froberta. Sub-UrethralTapeTreatment of Female Urinary IncontinenceMorbidityAssessment of the Trans-Obturator Route and a NewTape (I-STOP1):AMulti-Centre Experiment Involving 604 Cases. European Urology 47 (2005) 102-107.
Kutcher MJ, Ludlow JB, Samuelson AD, Campbell T, Pusek SN. Evaluation of a bioadhesive device for the management of aphthous ulcers. J Am Dent Assoc. Mar. 2001;132(3):368-376.
Li WZ, Zhao N, Zhou YQ, Yang LB, Xiao-Ning W, Bao-Hua H, Peng K, Chun-Feng Z. Post-expansile hydrogel foam aerosol of PG-liposomes: a novel delivery system for vaginal drug delivery applications. Eur J Pharm Sci. Aug. 30, 2012;47(1):162-169.
Bauer HW, Alloussi S, Egger G, Blümlein HM, Cozma G, Schulman CC; Multicenter UTI Study Group. A long-term, multicenter, double-blind study of an *Escherichia coli* extract (OM-89) in female patients with recurrent urinary tract infections. Eur Urol. Apr. 2005;47(4):542-548; discussion 548. Epub Jan. 21, 2005.
Mahalingam A, Smith E, Fabian J, Damian FR, Peters JJ, Clark MR, Friend DR, Katz DF, Kiser PF. Design of a semisolid vaginal microbicide gel by relating composition to properties and performance. Pharm Res. Nov. 2010;27(11):2478-2491.
North BB. A disposable adhesive patch for stress urinary incontinence. Fam Med. Apr. 1998;30(4):258-264.
Anita Patel, Khushbu Patel, Dr. Jayvadan Patel. Development and Evaluation of Mucoadhesive Vaginal Tablet of Sertaconazole for Vaginal Candidiasis. International Journal of PharmTech Research Oct.-Dec. 2011;3(4), 2175-2182.
Bakey WM. Predicting UTI in symptomatic postmenopausal women: a review of the literature. JAAPA. Aug. 2006;19(8):48, 50, 53-54.
A. Puratchikody, Prasanth V.V, Sam T. Mathew, Ashok Kumar B. Buccal Drug Delivery: Past, Present and Future—A Review. International Journal of Drug Delivery 3 (2011) 171-184.
Raz R. Urinary Tract Infection in Postmenopausal Women. Korean J Urol. Dec. 2011;52(12):801-808.
Foxman B, Gillespie B, Koopman J, Zhang L, Palin K, Tallman P, Marsh JV, Spear S, Sobel JD, Marty MJ, Marrs CF. Risk factors for second urinary tract infection among college women. Am J Epidemiol. Jun. 15, 2000;151(12):1194-205.
Foxman B. Recurring urinary tract infection: incidence and risk factors. Am J Public Health. Mar. 1990;80(3):331-3.
Sandri G, Rossi S, Ferrari F, Bonferoni MC, Muzzarelli C, Caramella C. Assessment of chitosan derivatives as buccal and vaginal penetration enhancers. Eur J Pharm Sci. Feb. 2004;21(2-3):351-359.
Sheldon HK, Gainsbury ML, Cassidy MR, Chu DI, Stucchi AF, Becker JM. A sprayable hyaluronate/carboxymethylcellulose adhesion barrier exhibits regional adhesion reduction efficacy and does not impair intestinal healing. J Gastrointest Surg. Feb. 2012;16(2):325-333.
Totsika M, Kostakioti M, Hannan TJ, Upton M, Beatson SA, Janetka JW, Hultgren SJ, Schembri MA. A FimH Inhibitor Prevents Acute Bladder Infection and Treats Chronic Cystitis Caused by Multidrug-Resistant Uropathogenic *Escherichia coli* ST131. J Infect Dis. Sep. 2013;208(6):921-928.
Wang L, Schnaare RL, Dezzutti C, Anton PA, Rohan LC. Rectal microbicides: clinically relevant approach to the design of rectal specific placebo formulations. AIDS Res Ther. Mar. 7, 2011;8:12.
Woolfson AD, Umrethia ML, Kett VL, Malcolm RK. Freeze-dried, mucoadhesive system for vaginal delivery of the HIV microbicide, dapivirine: optimisation by an artificial neural network. Int J Pharm. Mar. 30, 2010;388(1-2):136-143.
UTI in Postmenopausal Women. date unknown.
Thomas M Hooton, MD, Kalpana Gupta, MD, MPH. Recurrent urinary tract infection in women. Jan. 2, 2013.
C. Séné*, D. Neun, L. Tan-Sien-Hee, K. Ulman, Dow Corning (Life Sciences). Silicones as Excipients for Topical Pharmaceutical Applications. The Silky Touch Product Family from Dow Corning. 2002 Form No. 52-1034-01.
International Search Report of PCT/US2013/051544 filed on Jul. 22, 2013 pp. 1-15 (Oct. 23, 2013), Korean Intellectual Property Office, Republic of Korea.

* cited by examiner

FIG. 7A   FIG. 7B

COMPOSITIONS AND METHODS FOR PREVENTING INFECTIOUS DISEASES IN FEMALES

CROSS-REFERENCE TO RELATED APPLICATIONS

This application claims priority to Provisional Patent Application No. 61/673,769, filed on Jul. 20, 2012, and Provisional Patent Application No. 61/673,773, filed on Jul. 20, 2012, the entire contents of which are hereby incorporated by reference.

TECHNICAL FIELD

This disclosure is related to a material for preventing infectious disease in females, and more particularly, towards a material that may be embodied as a gel, film, balm, or other suitable material. The material may be applied over or about a urethral opening of the female.

BACKGROUND

Urinary tract infections (UTIs) are believed to be induced most frequently by direct inoculation of the urethra with gastrointestinal flora during sexual intercourse. The four leading risk factors for acute UTI are female sex, recent sexual intercourse, previous UTI, a new sexual partner, and history of urinary tract infection in a first-degree female relative. Anatomical considerations are believed to play a role in UTI heritability as shorter urethras and shorter distances between the urethra and the anus, provide less protection against cystitis compared to longer urethras.

Urinary tract infections are extremely common. UTI incidence was 0.70 episodes per person per year in a study of college women starting a new contraceptive method. Among young, healthy women with UTI, the infection recurs in 25% of women within 6 months. Urinary tract infections are also debilitating. Typical symptoms include urinary frequency, abdominal pain, fever, chills, and back pain. If untreated, symptoms can persist for 5-6 days and on average, women are bedridden for half of one day per UTI. Urinary tract infections also have considerable economic consequences.

3.5 billion USD is spent annually on UTI care including 8.6 million office visits in 2007 for UTIs in the U.S. alone. On average, one day of work or school is missed per UTI. Recurrent UTI is defined as a UTI within six months of a prior UTI. Approximately 7.5 million adult American women experience two or more UTIs per year. The current standard of care reflects the numerous challenges and unmet needs in the field. Acutely, symptoms are managed with broad-spectrum antimicrobials (such as fluoroquinolones). Following symptomatic improvement, nonantimicrobial strategies are implemented to prevent recurrence. These include urination soon after intercourse, liberal fluid intake, wiping front to back following defecation, and avoidance of tightfitting underwear. Cranberry products and D-mannose are often recommended despite very limited evidence that these interventions are efficacious and some evidence to suggest that the cranberry related treatments are actually damaging. If non-antimicrobial measures fail to prevent additional urinary tract infections, clinicians will often try systemic antimicrobial prophylaxis. Either post-coital or daily bedtime antimicrobial prophylaxis is prescribed (usually Bactrim or nitrofurantoin-are selected) with systemic exposure to the antimicrobial occurring for months if not years. This approach contributes to bacterial resistance and can induce noxious drug side effects.

Previous efforts to develop tools for urinary tract infection prophylaxis have focused on vaccine development. However, commercially available vaccines such as Uro-Vaxom and Solco Urovac have limited efficacy data, are expensive, and require frequent booster shots.

Given that the etiology of urinary tract infection is related to direct inoculation of the female urethra with gastrointestinal flora, it would be desirable to have a barrier that may have antimicrobial characteristics and be adhesive in nature when engaged with a person and that could be applied at the time of sexual intercourse that covered the urethral orifice, preventing bacterial access to the urethra, and could be removed after sexual intercourse A need therefore exists for a method or solution that addresses these disadvantages.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein is a method of providing preventative care to a female for reducing infectious disease. The method includes applying one of a bioadhesive and mucosadhesive material to either the urethral opening or periurethral area of a female.

According to one or more embodiments, applying a bioadhesive material includes applying a bioadhesive gel to prevent a urinary tract infection of the female.

According to one or more embodiments, the bioadhesive gel exhibits adhesive properties at or above 98 degrees Fahrenheit.

According to one or more embodiments, the bioadhesive gel further includes an antimicrobial agent.

According to one or more embodiments, the antimicrobial is an inorganic ion releasing material.

According to one or more embodiments, the bioadhesive material includes chitosan.

According to one or more embodiments, the chitosan is at least 80% deacetylated.

According to one or more embodiments, the chitosan is at least 90% deacetylated.

According to one or more embodiments, the bioadhesive material includes between 2.5% and 6% by weight of chitosan.

According to one or more embodiments, the bioadhesive material includes between 3.5% and 4.5% by weight of chitosan.

According to one or more embodiments, the bioadhesive material includes a high molecular weight polysaccharide.

According to one or more embodiments, the bioadhesive material includes an acidic solvent.

According to one or more embodiments, the acid solution is one of acetic acid and lactic acid.

According to one or more embodiments, the bioadhesive material includes between 1% and 7% by volume of lactic acid.

According to one or more embodiments, the bioadhesive material includes between 3% and 5% by volume of lactic acid.

According to one or more embodiments, the bioadhesive material includes glycerin.

According to one or more embodiments, the bioadhesive material includes between 5% and 25% by volume of glycerin.

According to one or more embodiments, the bioadhesive material includes between 10% and 20% by volume of glycerin.

According to one or more embodiments, the bioadhesive material includes one of aloe, vitamin E, Polyethylene Glycol (PEG), and Polyvinyl Alcohol (PVA), or combinations thereof.

According to one or more embodiments, the bioadhesive material includes alcohol.

According to one or more embodiments, the bioadhesive material includes a solvent.

According to one or more embodiments, the bioadhesive material includes between 1% and 18% by volume of alcohol.

According to one or more embodiments, the bioadhesive material is applied to both the urethral opening and periurethral area of a female.

According to one or more embodiments, a bioadhesive composition used for preventing urinary tract infections in a female is provided. The composition includes up to 3% lactic acid, between 10% and 30% glycerol, between 2% and 6% chitosan, and between 0% and 15% alcohol.

According to one or more embodiments, the composition includes between 15% and 25% glycerol.

According to one or more embodiments, the composition includes about 4% chitosan.

According to one or more embodiments, the composition exhibits adhesive properties at or above 98 degrees Fahrenheit.

According to one or more embodiments, the composition further includes an antimicrobial agent.

According to one or more embodiments, the antimicrobial is an inorganic ion releasing material.

According to one or more embodiments, the chitosan is at least 80% deacetylated.

In one or more embodiments, the chitosan is at least 90% deacetylated.

According to one or more embodiments, the composition includes a high molecular weight polysaccharide. In one or more embodiments, the molecular weight may be greater than 800,000.

According to one or more embodiments, the composition includes an acidic solvent.

According to one or more embodiments, the composition includes one of aloe, vitamin E, Polyethylene Glycol (PEG), and Polyvinyl Alcohol (PVA).

According to one or more embodiments, a method for making a bioadhesive precursor is provided. The method includes providing a first solution that includes a lactic acid solution and a polysaccharide, agitating the first solution, providing a second solution that includes glycerol and an alcohol to the agitated first solution to form a third solution, and agitating the third solution to form the bioadhesive precursor.

According to one or more embodiments, the first solution comprises about a 2% solution of lactic acid.

According to one or more embodiments, agitating the first solution includes at least one of mixing, shearing, and shaking.

According to one or more embodiments, agitating the first solution includes agitating the first solution to introduce air voids therein.

According to one or more embodiments, the method includes allowing the second solution to set for at least 24 hours for full dissolution.

According to one or more embodiments, the polysaccharide is chitosan.

According to one or more embodiments, agitating the third solution includes mixing.

According to one or more embodiments, the method includes providing the bioadhesive precursor in a packaging.

According to one or more embodiments, the bioadhesive precursor is processed to form one of a gel, film, ointment, and sponge structure.

According to one or more embodiments, the method includes sterilizing the packaging.

According to one or more embodiments, the method includes filtering the first solution.

According to one or more embodiments, a heating step is not provided.

According to one or more embodiments, a kit is provided. The kit includes a container, a bioadhesive composition in the container that includes chitosan, and an applicator for applying the bioadhesive composition.

According to one or more embodiments, the container is configured for a single dosage.

According to one or more embodiments, the composition exhibits adhesive properties at or above 98 degrees Fahrenheit.

According to one or more embodiments, the composition further includes an antimicrobial agent.

According to one or more embodiments, the antimicrobial is an inorganic ion releasing material.

According to one or more embodiments, the chitosan is at least 90% deacetylated.

According to one or more embodiments, the composition includes a high molecular weight polysaccharide.

According to one or more embodiments, the composition includes an acidic solvent.

According to one or more embodiments, the composition comprises one of aloe, vitamin E, Polyethylene Glycol (PEG), and Polyvinyl Alcohol (PVA).

According to one or more embodiments, the composition is applied to both the urethral opening and periurethral area of a female.

According to one or more embodiments, a product is provided. The product includes a mucoadhesive material on one side of the product for positioning about the urethral opening of a female and a water impermeable barrier layer on an opposing side of the product for preventing infectious disease transfer to the urethral opening.

According to one or more embodiments, the product is one of a pad, sponge, or film.

According to one or more embodiments, a method of applying the product is provided and includes positioning the pad into engagement about the urethral opening and the periurethral space of a female.

According to one or more embodiments, a product is provided and includes a bioadhesive treatment solution for prevention of infectious diseases in the urinary tract of a female, the solution comprising chitosan.

According to one or more embodiments, a method of providing preventative treatment is provided. The method includes providing a pad having a bioadhesive surface on one side thereof and a flap defined on a circumference thereof, and positioning the pad over the urethral opening of a patient and extending the flap into the vaginal opening.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings:

FIG. 7A is a top view of a pad for use in preventing infectious diseases in females according to one or more embodiments disclosed herein;

FIG. 7B is a top view of a pad for use in preventing infectious diseases in females according to one or more embodiments disclosed herein;

DETAILED DESCRIPTION

Figure 1:
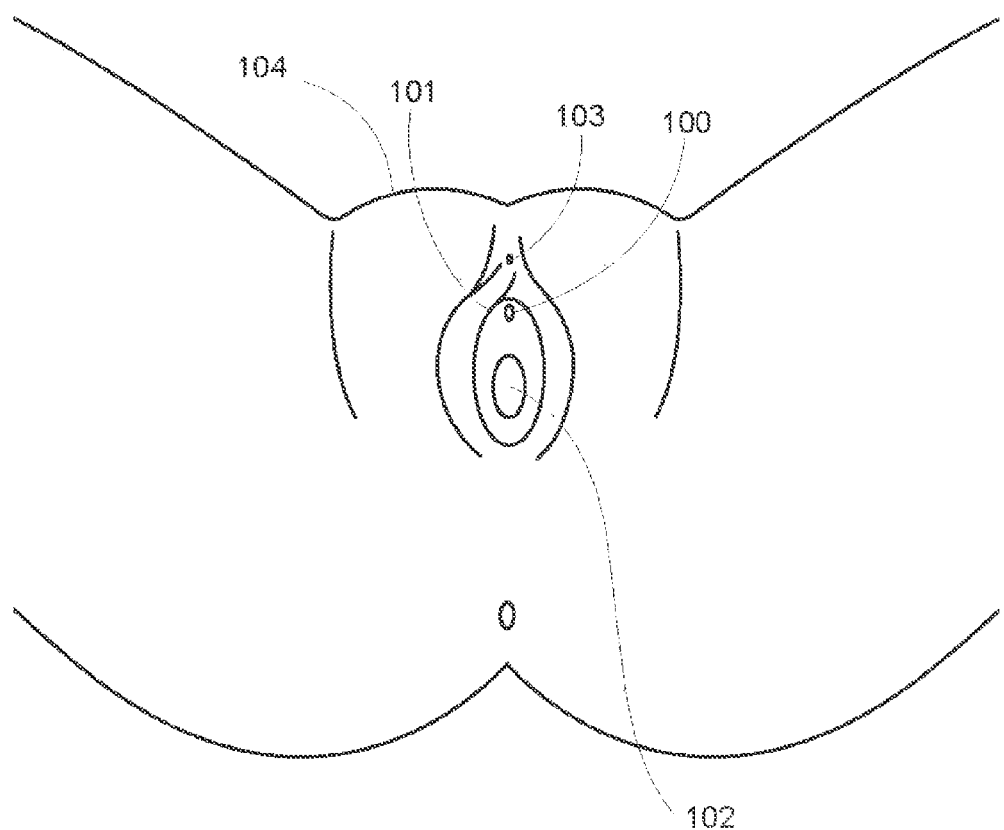
FIG. 1 is a front anatomical view of a female anatomy.

The presently disclosed subject matter is described with specificity to meet statutory requirements. However, the description itself is not intended to limit the scope of any subject matter presented herein. Rather, the inventors have contemplated that the claimed invention might also be embodied in other ways, to include different steps or elements similar to the ones described in this document, in conjunction with other present or future technologies.

The one or more embodiments of methods, products, and systems disclosed herein relate to the prevention of urinary tract infections using a bio compatible barrier with or without anti-microbial characteristics in the form of a gel, cream, balm, and the like applied to the urethral opening and periurethral space prior to sexual intercourse. As a significant majority of urinary tract infections are believed to be the result of inoculation of gastrointestinal tract bacteria, primarily E. coli, directly into the opening of the urethra, a barrier that prevents the urethra from contacting bacteria deposited in and around the urethral area during sex may prevent the sequellae of urinary tract infections.

One or more embodiments disclosed herein include preformed gels and compositions applied to the urethral opening and periurethral area prior to sexual intercourse. Given the moistness of the periurethral area prior to and during sexual intercourse, any pre-formed barrier gel or other subject matter disclosed herein may be advantageously provided with bioadhesive and/or mucoadhesive properties.

Bioadhesive gels and compositions may be utilized because these gels exhibit excellent tack when applied to wet mucosal surfaces. They tend to be hydrophilic with relatively low cohesive strength. A wide range of bioadhesive gels may be utilized with the subject matter disclosed herein. For example, a bioadhesive such as those that include compositions of slightly cross-linked polyacrylic and polymethacrylic acids as well as blends of hydrophilic cellulose derivatives and polyethylene glycol (PEG) may be utilized. Additionally, bioadhesive gels that may be utilized with the subject matter disclosed herein may include, but are not limited to, cellulose-derivatives, hyaluronic acid and derivatives, pectin and traganth, starches, sulfated polysaccharides, carrageenan, alginates and gelatin, and combinations thereof.

An example of a gel and/or composition that may be advantageously used with the subject matter disclosed herein includes a family of tunable bioadhesive copolymer hydrogels of thermoresponsive poly(N-isopropyl acrylamide) containing zwitterionic poly sulfobetaine. These gels are highly bioadhesive at 37 degrees Celsius, but decrease in bioadhesiveness below 25 degrees Celsius. Therefore these gels may be applied to the urethral opening and periurethral area with elevated bioadhesive properties due to the temperature of the female to which the gel is applied. These hydrogels exhibit meaningful antimicrobial activity when they are incubated with Grampositive bacteria (S. epidermidis) and Gram-negative bacteria (E. coli). When exposed to temperatures below body temperature, these gels lose bioadhesiveness and can be removed from mucosal and skin surfaces.

Hyalobarrier (available from Fidia Advanced Biopolymers, AbanoTerme, Italy) includes an aqueous gel of ACP200 which is an auto-cross-linked ester of hyaluronic acid. The gel is a highly effective barrier for protecting and separating tissues and exhibits considerable bioadhesion to mucosal surfaces. In one or more embodiments, Rebasol (available from EMCM, Nijmegen, The Netherlands), a bioresorbable gel formed of ultra-pure alginate and poly-dextran sulphate, may be employed. The muco-adherent properties of the gel allow it to remain in place even in gravitationally dependent areas. This advantageously allows for these gels to be applied to the urethral opening and periurethral area prior to sexual intercourse and can be removed following intercourse using soap and water. As these materials are bioresorbable, they will only transiently obstruct the GU tract even if they are not manually removed with soap and water or another solvent system.

Numerous barrier hydrogels that can be formed in situ are known in the art and are applicable to the urinary tract infection prevention products, techniques, methods, and the like disclosed herein. In situ hydrogel systems include injectable fluids that can be placed into or onto the body and then gel or solidify secondary to an endogenous chemical reaction or an exogenous trigger such as temperature, pH, salt concentration, the presence of electromagnetic radiation and/or other triggers. Either a physical or chemical change can result in in situ gelation.

Several possible products, manners, mechanisms, and the like leading to in situ implant formation may be employed. For example, a solvent exchange approach includes dissolving a water-insoluble polymer in a water-miscible, biocompatible solvent. Upon contact with body fluids, the solvent diffuses out of the polymer while water permeates the liquid polymer matrix. Due to its insolubility in water, the polymer precipitates, resulting in the formation of a solid polymeric implant.

In situ forming gels that are activated by physiological conditions and are not formulated with organic solvents or copolymerization may also be employed. Gelation can occur in situ after a change in pH, by ionic cross-linking, or secondary to a temperature-induced phase transition.

The solubility of some polymers can radically change in response to increases in ambient temperature (lower critical solution temperature, LCST). This functionality is the result of a balance between hydrophilic and hydrophobic moieties on the polymer chain and the free energy of mixing. Due to their temperature dependence, hydrogen bonds and hydrophobic effects contribute to the observed temperature-sensitive phase transitions. At the LCST, polymer-polymer and water-water interactions become more favorable than hydrogen bonding between the polymer and water.

Therefore, an abrupt transition occurs as the solvated macromolecule quickly dehydrates and changes to a more hydrophobic structure. Alternatively, some amphiphilic polymers, that self-assemble in solution, show micelle packing and gel formation because of polymer-polymer interactions when temperature is increased. Temperature sensitive, in situ forming gel systems can be created using polysaccharides, N-isopropylacrylamide (NIPAM) copolymers, poly(ethylene oxide-b-propylene oxide-b-ethylene oxide) (PEO-PPOPEO) and its copolymers, poly(ethylene oxide)/(D,L-lactic acid-co-glycolic acid) (PEO/PLGA) copolymers, and thermosensitive liposome based systems.

Gels applied to the urethral opening and periurethral area may prevent bacterial infection by serving as a barrier to bacterial translocation. However, barrier hydrogels may be formulated with antimicrobial agents that could contribute a second anti-infective mechanism of action. Numerous antimicrobials that can be formulated with hydrogels for long term release may be applied as part of the product, system, techniques, methods, and the like described herein. Numerous relevant antimicrobial agents may include triclosan, riclocarban/Trichlorocarbamide, PCMX/Chloroxylenol, selenium, and inorganic ions such as silver, zinc and copper. In one or more embodiments, Chlorhexidine Gluconate (CHG) may be used as an antimicrobial.

In one or more embodiments, applicators designed to deliver a precise volume of gel, cream, or balm to the urethral opening and the periurethral space may be provided and will be described in further detail.

As illustrated in FIG. 1, the female urethra 100 is located behind the labia minora 101, anterior to the vaginal orifice 102, and posterior to the clitoris 103. In its collapsed state, the female urethra measures about 6 mm in diameter. During intercourse, it can be surrounded by secretions that lubricate the space around the urethra, referred to herein as the periurethral space or periurethral area. Although there can be considerable anatomical variation between women, the urethral opening is substantially circular with a diameter typically in the range of between 4 and 5 mm. The periurethral area is a roughly triangular surface bounded anteriorly by the clitoris, laterally by the labia minora, and posteriorly by the vagina. It has an approximate surface area of 4 square centimeters.

Figure 2:
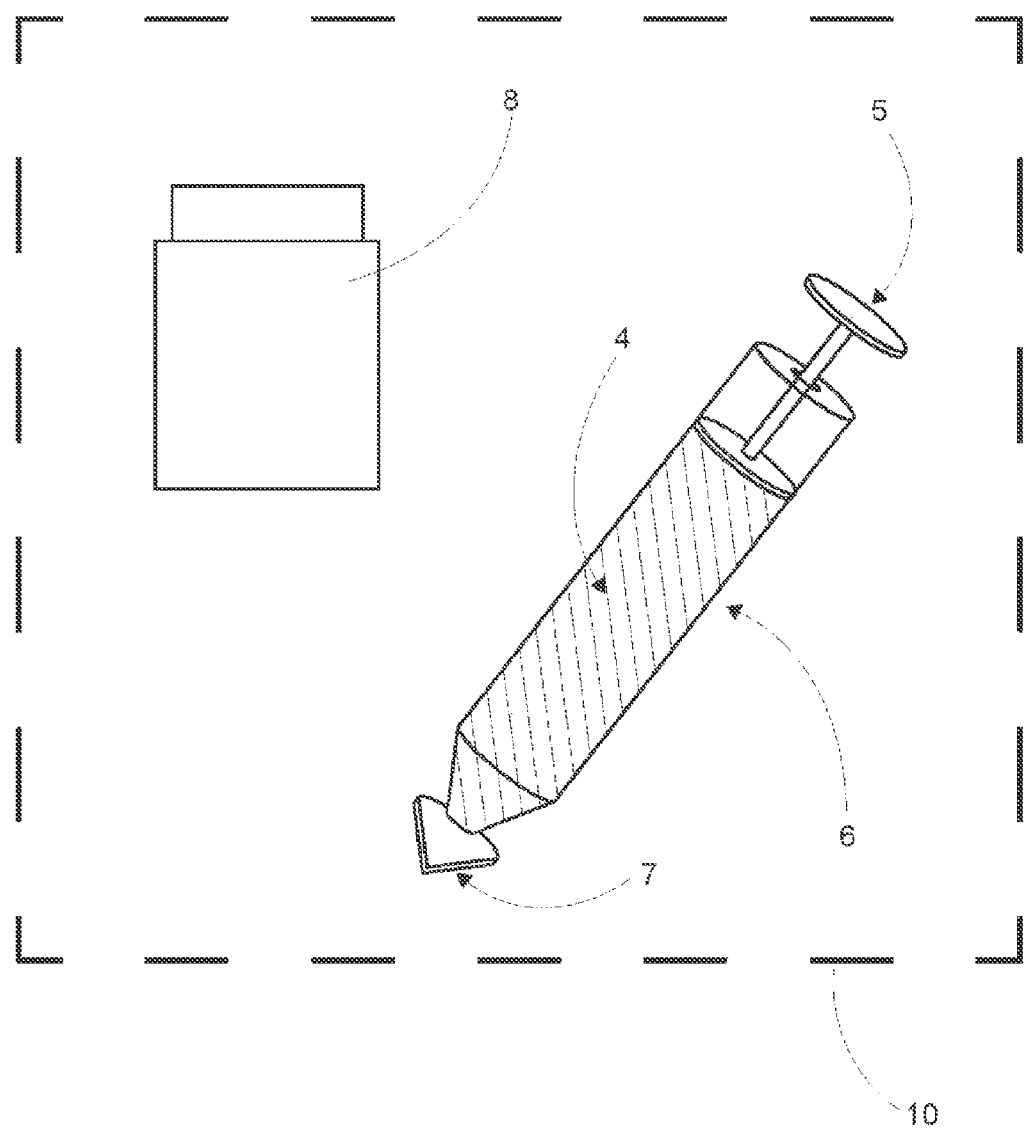
FIG. 2 is a view of a kit according to one or more embodiments disclosed herein.

An example applicator with a triangular applicator tip is depicted in FIG. 2 as part of a kit 10. The kit 10 may include a container 8 that includes a gel 4 that is formed according to the one or more methods disclosed herein. A syringe 6 may be used to transport gel 4 from the container 8 to a treatment site. Plunger 5 can be depressed resulting in the extrusion of a fixed volume of gel 4 through aperture 7 which can be pressed against the urethral opening and periurethral space by the user. The aperture 7 may be formed at a dispensing end of the syringe 6 and may define a prism shape as shown. The dispensing end should have a surface area between 1 and 8 square centimeters to accommodate anatomical variation between women. Sufficient gel 4 should be extruded to form a barrier on the female that has a thickness between 1 mm and 1 cm following application of the barrier gel. A barrier gel could also be sprayed onto the urethra and periurethral space using a spray based applicator including gel-containing aerosols.

In one or more embodiments, gel and/or composition 4 may be a temperature sensitive hydrogel that includes a Poly (NIPAAm-co-SBMA) system with a lower critical solution temperature of approximately 25 degrees Celsius. As used herein, gel may also be referred to as a composition. Many of the properties disclosed herein relating to the gel will be equally applicable to any material made from the compositions disclosed herein. In one or more embodiments, an antimicrobial agent such as silver nanoparticles may be loaded into the gel, which may be a hydrogel. The resulting hydrogel formulation can then be loaded into the syringe applicator 6. Prior to sexual intercourse, a female may apply sufficient hydrogel to her urethral opening and periurethral space to form a gel barrier that is at least about 1 mm thick and that is bioadhesive at 37 degrees Celsius. Following sexual intercourse, the female may apply cold water (temperature at 25 degrees Celsius or below) to the vulva to reduce the bioadhesiveness of the gel and eliminate the barrier gel from her skin/mucosa. The gel 4 is configured to remain in place over the urethra despite the presence of secretions and any forces encountered during sexual intercourse.

The vagina produces secretions during sexual intercourse that are between a pH of 3.8 and 4.5, creating a lubricious, acidic environment in the periurethral space potentially inhospitable to an adhesive film. The skin overlying the mons pubis area 104 illustrated in FIG. 1, however, generally remains dry. Mucoadhesion is generally achieved through the formation of non-covalent bonds between a polymeric substance and the mucosal surface. Hydrogen bonding is an important component of these noncovalent forces and is facilitated in the presence of protonated groups, especially carboxylic acid moieties. In the absence of hydrogen bonding (e.g. in the presence of de-protonated carboxylic acid moieties), hydrogen bonding can no longer take place, and the mucoadhesive force wanes. Typically, carboxylic acid moieties have a pKa of between 2 and 4. Those moieties with pKas closer to 4 will have more protonation in the presence of vaginal secretions and will facilitate more hydrogen bond formation. Ideally, a mucoadhesive film used to create a barrier over the urethra during sexual intercourse should maintain strong mucoadhesion in the presence of vaginal secretions or low pH lubricant and be removable after intercourse in the presence of a higher pH substance (e.g. soap and tap water), disruptive forces (e.g. vigorous scrubbing), or a solvent that solubilizes the mucoadhesive.

Figure 3A:
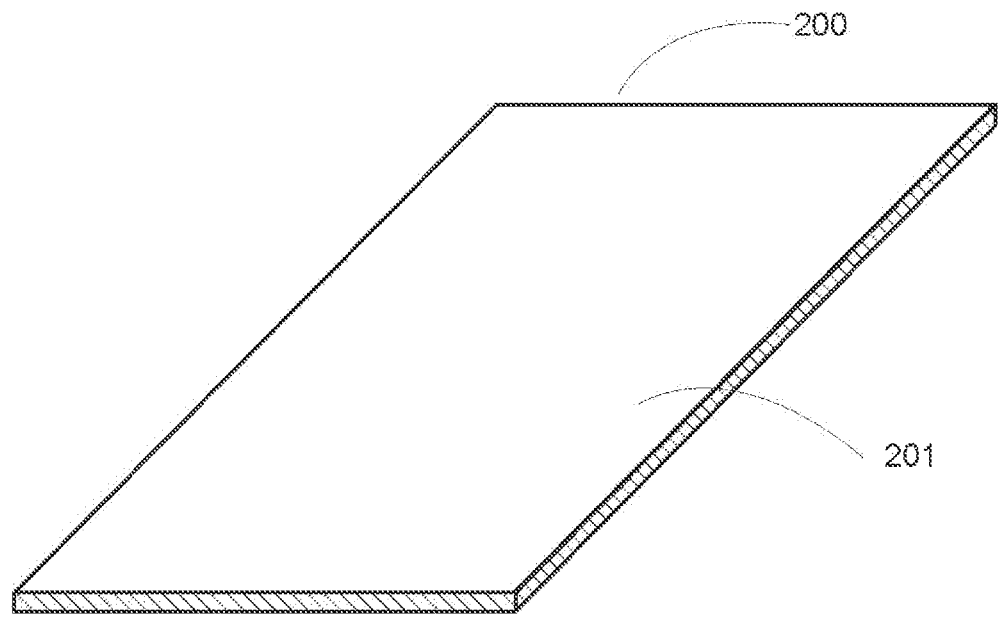
FIG. 3A is a perspective view of a pad for use in preventing infectious diseases in females according to one or more embodiments disclosed herein.
Figure 3B:
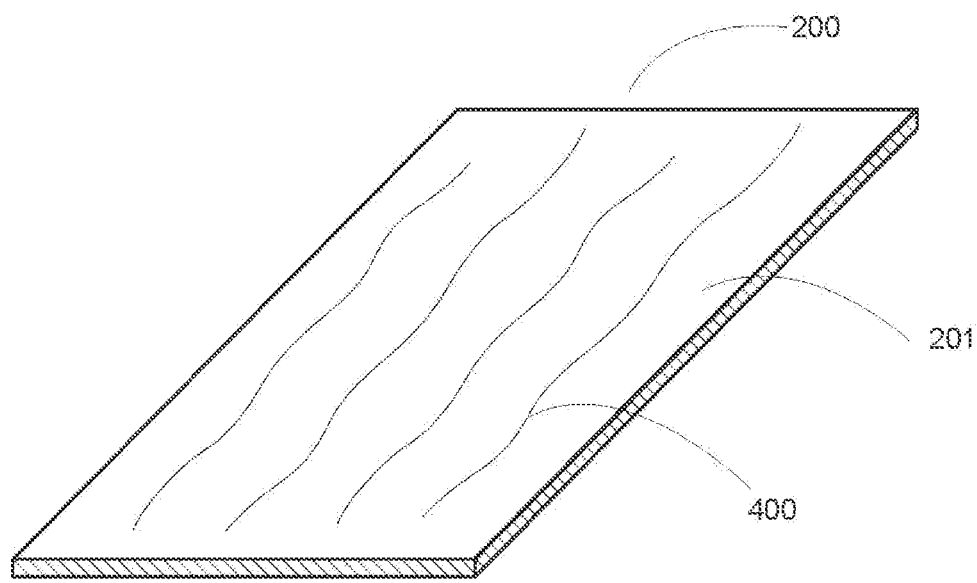
FIG. 3B is a perspective view of a pad for use in preventing infectious diseases in females according to one or more embodiments disclosed herein.

In one or more embodiments, an adhesive product, such as adhesive film 200 as is illustrated in FIG. 4A may be provided for preventing the spread of infection such as a urinary tract infection. The film 200 may also be a pad or sponge and is configured for being place into engagement about the urethral opening and the periurethral space of the female. A hydratable mucoadhesive base layer 201 is created from a biocompatible, hydratable, but water insoluble polymer such as polycarbophil, hydroxyl propyl cellulose, poly(vinyl pyrrolidone), carboxymethyl cellulose, hydroxyl propyl methyl cellulose, hydroxyl ethyl cellulose, poly(vinyl alcohol), cross-linked poly(acrylic acid), and/or combinations thereof. Layer 201 may also include naturally occurring polysaccharide gums, alginates, or chitosan. Layer 201 may include any of the compositions disclosed herein. This base layer may be created using a solvent evaporation or solvent casting technique, leading to a thickness of between 0.001 and 0.1 inches. In one or more embodiments, base layer 201 is maximally adhesive to the periurethral mucosa during sexual intercourse (e.g. in the presence of acidic vaginal secretions) but non-adhesive (i.e. removable) at higher pHs (e.g. a solution of bath soap and tap water). Lightly cross-linked poly(acrylic acid) or poly(methacrylic acid) represents an advantageous substance for base layer 201 as it is likely to be protonated in the presence of vaginal secretions (i.e. mucoadhesive) but deprotonated (i.e. non-mucoadhesive) at higher pHs (e.g. after intercourse in the presence of soap and water). One such polymer is poly(acrylic acid) cross-linked with 0.3% w/w divinyl glycol (polycarbophil) which shows maximal mucoadhesion between pH of 3 and 6 and very poor mucoadhesion at a pH greater 7. This material can also be cast into between about a 130 um and about a 150 um film. In other embodiments, base layer 201 is further impregnated with an antimicrobial agent or biosurfactant 400 as illustrated in FIG. 3B.

Figure 4:
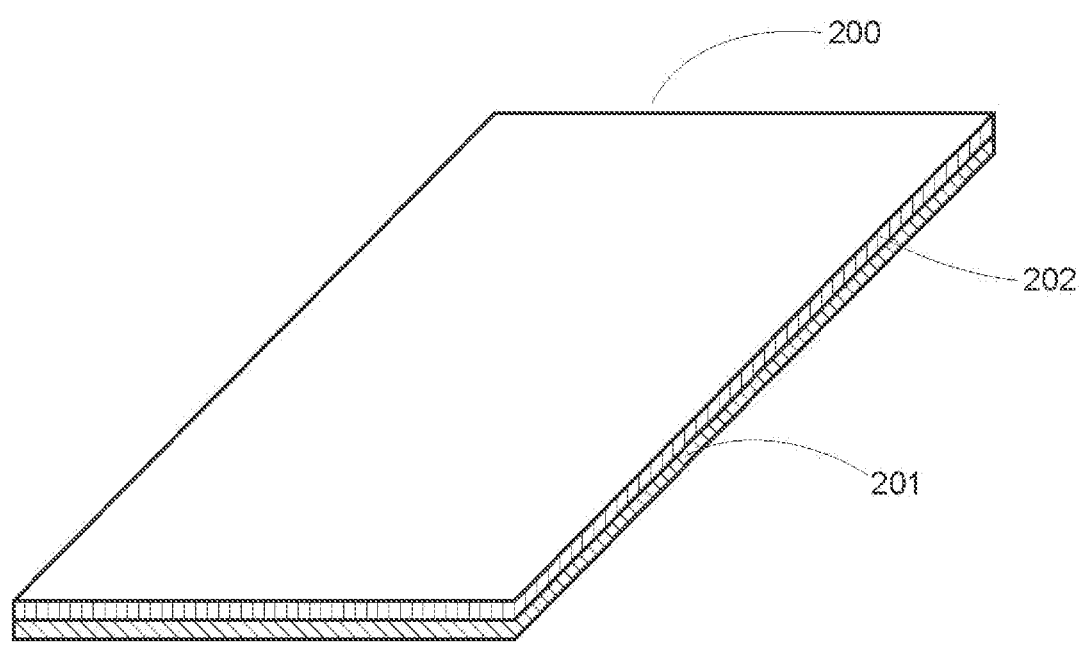
FIG. 4 is a perspective view of a pad for use in preventing infectious diseases in females according to one or more embodiments disclosed herein.

In another embodiment of adhesive film 200, as illustrated in FIG. 4, a hydratable mucoadhesive base layer 201 is applied to a water impermeable barrier layer 202. Layer 202 may include a water impermeable material such as latex, silicone, polyurethane, PTFE, cellulose, melted pharmaceutical wax, or polypropyelene and is meant to further protect the mucoadhesive layer from vaginal secretions and forces exerted during sexual intercourse. Layer 201 is fabricated as described above and is then laminated onto a water impermeable barrier layer 202 using solvent casting, spraying, extrusion, or physical pressing. Layer 202 may be advantageously provided as soft, water impermeable, and resistant to chemical modification or abrasion. Examples of such materials that may be utilized may include melted Dentsply Utility Wax (available from Patterson Dental of St. Paul, Minn. USA), biaxially oriented polypropylene (BOPP) (available from Griff Paper & Film of Fallsington, Pa. USA), ETHOCEL, WALOCEL, and METHOCEL (available from Dow Wolff Cellulosics of Midland, Mich. USA). In one or more embodiments, water impermeable barrier layer 202 may also include a plasticizer. In one or more embodiments, base layer 201 may be further impregnated with an antimicrobial agent or biosurfactant. For example, a mucoadhesive bilayer patch containing chitosan mucoadhesive impregnated with nifedipine or propanalol laminated onto a plasticized ethylcellulose backing using a solvent casting and drying approach may be employed.

Figure 5:
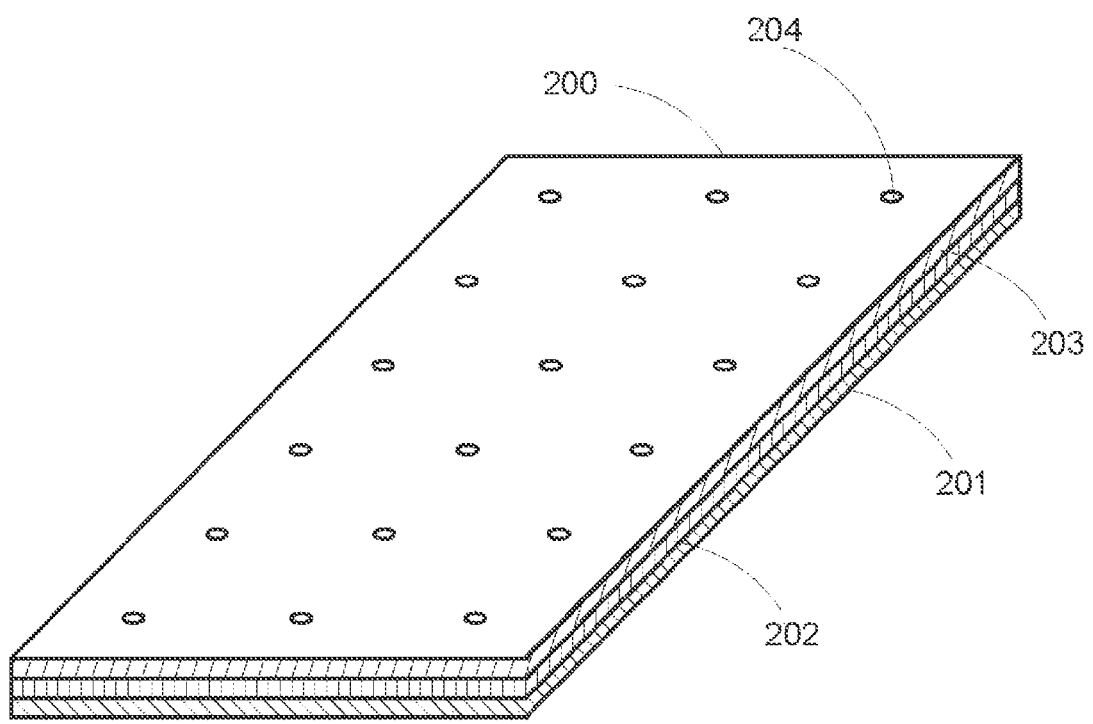
FIG. 5 is a perspective view of a pad for use in preventing infectious diseases in females according to one or more embodiments disclosed herein.

In another embodiment of adhesive film 200, as illustrated schematically in FIG. 5, a water impermeable barrier layer 202 may be positioned between a hydratable mucoadhesive base layer 201 and a drug reservoir layer 203. The drug reservoir layer 203 may include a matrix containing a combination of insoluble and soluble excipients and a dehydrated hydrogel 204 impregnated with a drug. Insoluble excipients may include cellulose or cellulosic derivatives (hydroxy propyl methyl cellulose, methyl cellulose, or ethyl cellulose, carboxymethyl cellulose). Soluble excipients may include lactose, sorbitol, xylitol, mannitol, amylose, malic acid, ascorbic acid, succinic acid, polyethylene glycols, poly(vinyl pyrrolidones), and gelatins. Dehydrated hydrogels suitable for this application include polyoxyalkylene block copolymers, hydroxyethyl methacrylate homopolymers, hydroxyethoxyethyl methacrylate homopolymers, hydroxydiethoxyethyl methacrylate homopolymers, methoxyethyl methacrylate homopolymers, methoxydiethoxyethyl methacrylate homopolymers, ethylene glycol dimethacrylatehomopolymers, N-vinyl 2-pyrrolidone homopolymers (PVP), methacrylic acid hompolymers, vinyl acetate homopolymers, copolymers of the foregoing monomers, alginic acid, polyethylene oxide)/propylene oxide copolymers with alginic acid, polyvinyl alcohol, and the like. In some embodiments, the dehydrated hydrogels are impregnated with antimicrobial agents or biosurfactants.

Each of the products 200 are configured to be applied to the mons pubis area 104 and extend over the urethra 100. Each of the products 200 may include any of the compositions disclosed herein.

Figure 6:
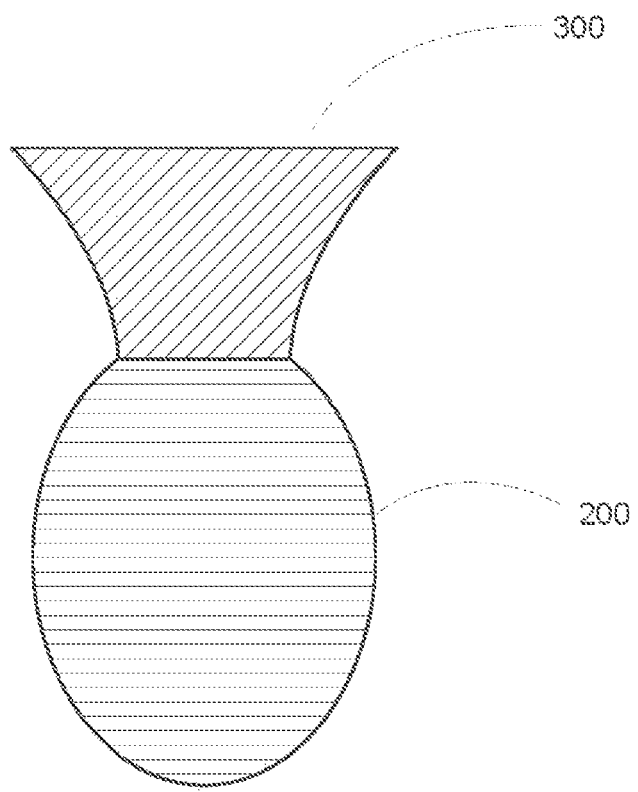
FIG. 6 is a top view of a pad for use in preventing infectious diseases in females according to one or more embodiments disclosed herein.

In yet another embodiment, adhesive film 200 may be attached to a skin adhesive patch 300 as illustrated in FIG. 6. Skin adhesive patch 300 (designated by the area defined by the diagonally extending cross hatching) can be affixed to the skin anterior to the labia majora in the region of the mons pubis. This area frequently remains dry during intercourse and when adhered to adhesive patch 300, assists in anchoring adhesive film 200 in place over the periurethral space. The skin adhesive may be made from acrylics. One such skin adhesive is the Tegaderm™ (available from 3M of St. Paul, Minn. USA).

As a specific example, an adhesive film for the prevention of bacterial entry into the urethra can be fabricated by creating a trilaminate film consisting of a water impermeable barrier layer sandwiched between a hydratable mucoadhesive base layer and an antimicrobial reservoir layer. The hydratable mucoadhesive base layer is made from poly(acrylic acid) cross-linked with 0.3% w/w divinyl glycol (polycarbophil) which shows maximal mucoadhesion between a pH of 3 and 6. An ethylcellulose water impermeable barrier layer is disposed on top of the mucoadhesive base layer using solvent casting and drying. An antimicrobial reservoir layer that includes a polyoxyalkylene block copolymer with alginic acid impregnated with an antimicrobial agent (e.g. silver nanoparticles) can be disposed on top of the water impermeable barrier layer using solvent casting or drying. A skin adhesive polyurethane patch lined with an acrylic adhesive (e.g. a Tegaderm™ patch available from 3M of St. Paul, Minn. USA) can be affixed to the impermeable barrier layer either through direct adhesion or a joining technology like heat-sealing or RF welding to provide an attachment site for the adhesive film on to the dry skin of the mons pubis before sexual intercourse. After sexual intercourse is completed, the adhesive film can be dissolved in soap and tap water and the skin adhesive patch can be peeled off the skin overlying the mons pubis and discarded.

Figure 7C:
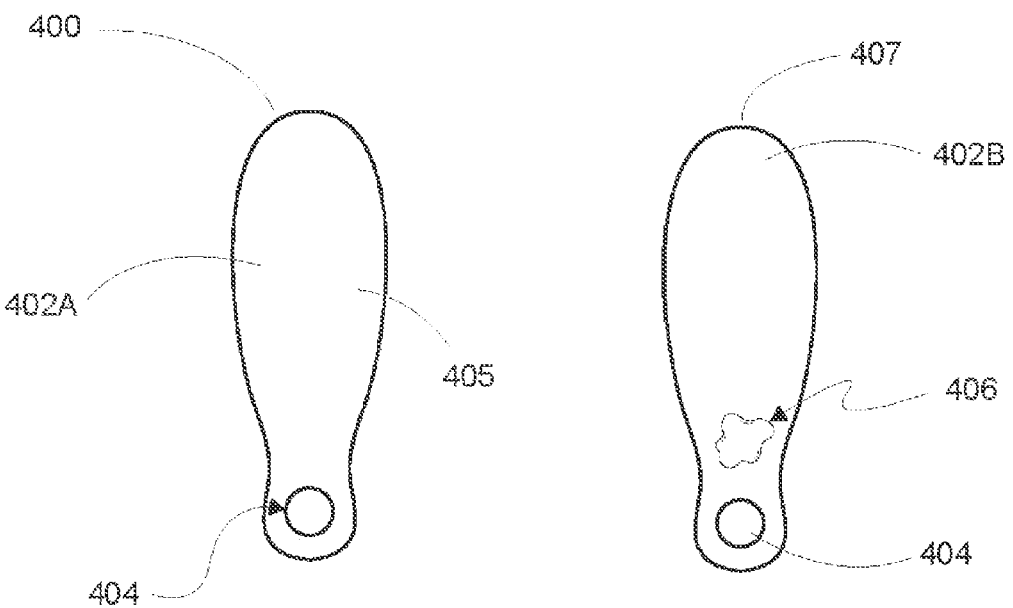
FIG. 7C is a side view of a pad installed about a female for use in preventing infectious diseases in females according to one or more embodiments disclosed herein.
Figure 7C:
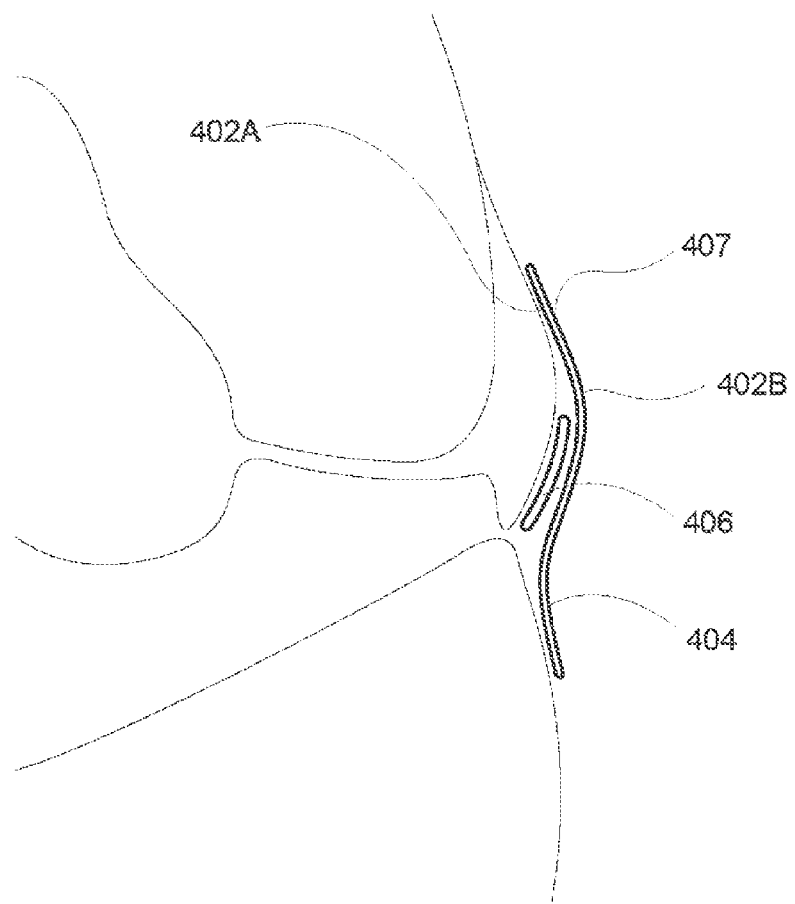

A pad is illustrated in FIGS. 7A, 7B, and 7C and is generally designated 400. The pad 400 includes a surface 402A on one side and an opposing surface 402b on the other. Surface 402A may include one of a bioadhesive and/or mucoadhesive 405. An opening 404 is defined on one end of the pad 400 for being positioned over the vaginal opening. A pull tab 407 is defined at an upper end of pad 400. The pad 400 is positioned over the vaginal area such that a portion of gel material 406 defined on the 402A surface is positioned proximal the urinary tract and acts as a barrier for infectious transfer. The pad 400 is removed by pulling on tab 407.

Figure 8:
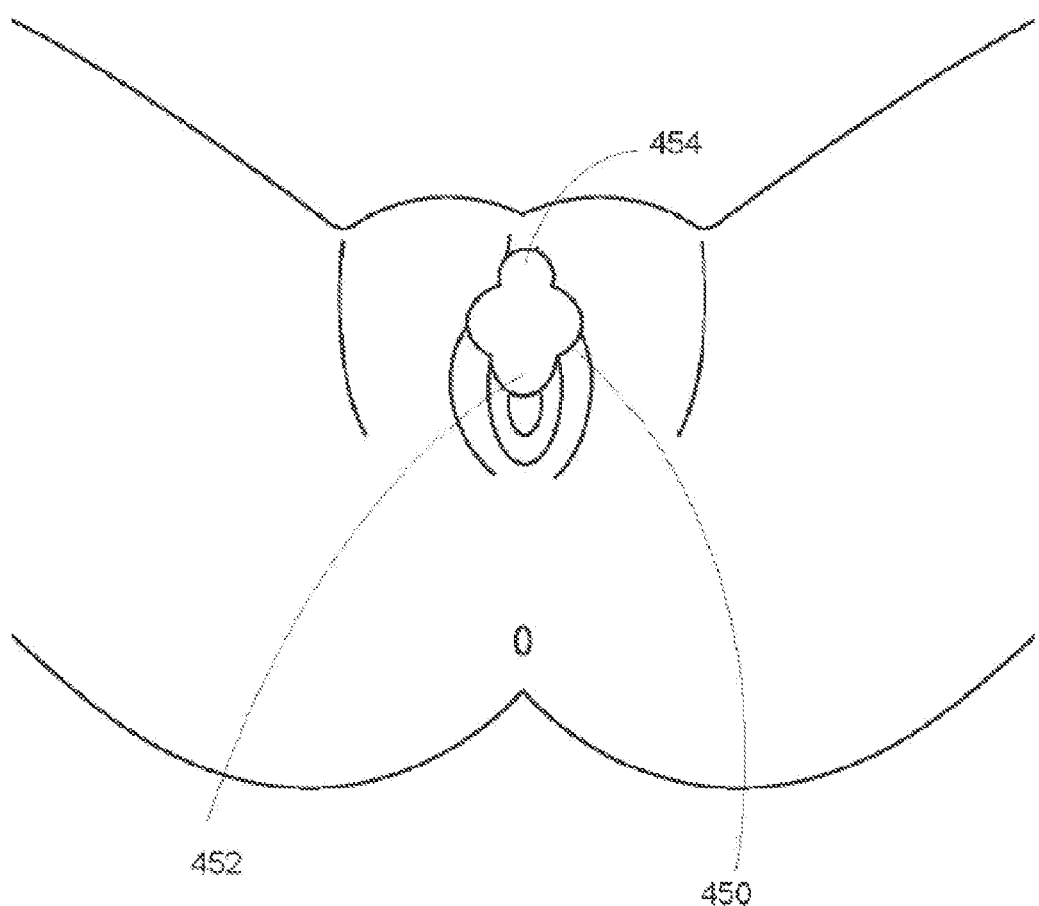
FIG. 8 is a side view of a pad installed about a female for use in preventing infectious diseases in females according to one or more embodiments disclosed herein.

FIG. 8 illustrates a patch 450 configured for being installed about the urinary tract of a female. The patch 450 may have a mucoadhesive or bioadhesive side that faces and engages with the female, and may further include a tab 452 that is configured for insertional engagement into the vaginal opening of the female. Tab 452 may be folded inwardly into engagement with the vaginal opening about crease 456. The patch 450 is installed in a similar manner to the one or more products disclosed herein, and is removed by grasping tab 454 and pulling the patch 450 out of engagement with the female.

Figure 9:
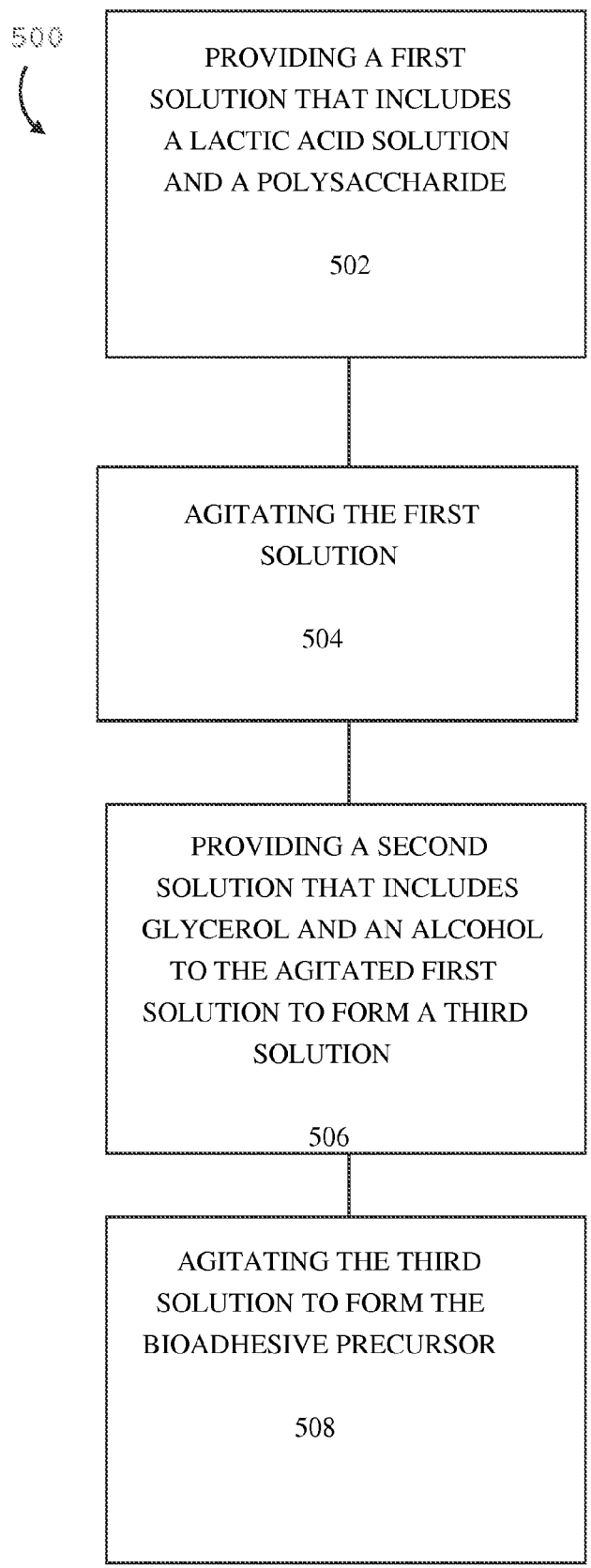
FIG. 9 is a flowchart depicting one or more methods for making a precursor that forms a gel, balm, film, or other medium for use in preventing infectious diseases in females according to one or more embodiments disclosed herein.

One or more methods for making a bioadhesive precursor and/or composition are illustrated in the flowchart of FIG. 9 and are generally designated as 500. The precursor may be formed into a gel, balm, film, ointment, sponge, or the like for use in preventing the spread of infection, such as, for example, a urinary tract infection in a female. The bioadhesive may exhibit adhesive properties at a range of temperatures consistent with the temperature of the female body. For example, the bioadhesive may exhibit adhesive properties at or about 98 degrees Fahrenheit.

The one or more methods 500 may include providing a first solution that includes lactic acid solution and a polysaccharide 502. The lactic acid may be between a 1% and 7% by volume of the solution. In one or more embodiments, the lactic acid may be a 2% solution of lactic acid. The lactic acid solution may be made from an 88% solution and distilled water. Lactic acid may be provided due to efficiency as a solvent for the polysaccharide. Additionally, lactic acid may be provided due to an increase in antimicrobial and healing benefits that the presence of lactic acid has on the polysaccharide. Alternatively, any appropriate acidic solution or solvent for polysaccharides may be employed, such as, for example, acetic acid. Additionally, caprolactone may be utilized as a complement to the acidic solution of the acetic acid.

The polysaccharide may be any appropriately provided high molecular weight polysaccharide. In one or more embodiments, the polysaccharide may be chitosan. The chitosan may be formed into flakes of solid material. Chitosan may be formed from de-acetylated chitin. For example, the chitosan may be at least 85% de-acetylated. In one or more embodiments, the chitosan may be 90% de-acetylated. A desired quantity of chitosan flakes may be measured and then the lactic acid solution is added to the flakes. The chitosan may be between 2.5% and 6% by weight in the solution. In one or more embodiments, the chitosan may be 4% by weight in the solution.

The method 500 may include agitating the first solution 504. Agitating the first solution 504 may include any appropriate form of agitation, including, but not limited to, mixing, shearing, and shaking. The agitation may include agitating the solution to introduce air voids in order to develop a solution having a desirable amount of froth. The first solution may also be filtered with fine mesh, centrifuge or any other appropriately provided filtering method.

The method 500 may include providing a second solution that includes glycerol and an alcohol to the agitated first solution to form a third solution 506. The glycerol may be between about 5% and about 25% glycerin. The alcohol may be between 1% and 18% by volume in the solution. The alcohol may be medical grade quality and may be advantageously provided to mask the scent of the polysaccharide. The third solution may be allowed to set for 24 hours for full dissolution. In one or more embodiments, the third solution may reach full dissolution in a lesser amount of time. The glycerin may be provided to help maintain moisture content in the gel as the polysaccharide can be absorptive.

The one or more methods 500 may include agitating the third solution to form the bioadhesive precursor 506. Agitating the third solution may include mixing.

The one or more methods 500 may include providing the bioadhesive precursor as a final product such as a gel, ointment, film, sponge, and the like in a packaging. The packaging may be a blister pack, sealed foil, vacuum packed, or any other appropriate form of packaging. Further processing may be performed before packaging, such as, for example, sterilizing the packaging. Sterilization may be accomplished with an electronic beam processing. The sterilization may be of the secondary packaging, which might include a blister pack or sealed foil, and the primary packaging into which the secondary packaging is contained.

The packaging may be configured for single dosage application and may be embodied in a kit that includes a container, the bioadhesive placed in the container, and an applicator, such as syringe 6, plegdet or spatula for applying the adhesive.

The one or more methods 500 may be accomplished without application of heat.

A method of providing preventative care to a female for reducing infectious disease utilizing or more of the materials disclosed herein may include applying the one or more materials disclosed herein such as the gel, balm, ointment, and the like having a bioadhesive and/or mucoadhesive property to either or both of the urethral opening and periurethral area of a female. In this manner, the material acts as a barrier that prevents the spread of infection into the urinary tract of the female.

The one or more methods of providing preventative care to a female may utilize a bioadhesive gel made from a composition disclosed herein. One example of the gels disclosed herein may include up to 3% lactic acid, between 10% and 30% glycerol, between 2% and 6% chitosan, and between 0% and 15% alcohol. The bioadhesive gel may include an acid solvent such as is disclosed herein. The bioadhesive gel may further include one of aloe, vitamin E, Polyethylene Glycol (PEG), and Polyvinyl Alcohol (PVA). In one or more experiments, the viscosity average molecular weight was calculated as 910,000.

Application of the bioadhesive gel may include the female washing and sterilizing their hands. The female then removes the cap or other enclosure manner of the container and applying a full amount of the bioadhesive gel to the primary index finger. The female then locates the top opening of the vaginal introitus, spreads the labia, and then applies the gel around the urethra meatus. After intercourse, the gel is removed by washing with soap and water or any other appropriately provided biocompatible organic solvent. Urination may also be sufficient to remove the gel.

In one or more experiments, the viscosity of the gel and/or composition was measured with a Brookfield DV viscometer at 25 degrees Celsius and with a #7 spindle. At 20 revolutions per minute (rpm), a viscosity of 290,000 centipoise (cp) was measured. At 50 rpm, a viscosity of 143,200 cp was measured. At 100 rpm, a viscosity of 89760 cp was measured. This is known as pseudoplastic flow behavior, the higher the fluid is sheared, the lower the viscosity (shear thinning) and is typical of these types of polymer solutions.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A method of providing preventative care to a female for reducing infectious disease, the method comprising prior to sexual intercourse applying one of a bioadhesive and mucosadhesive material comprising chitosan to the urethral opening and periurethral area of a female to form a barrier over the urethral opening to prevent the spread of infection into the urinary tract of the female during the sexual intercourse.

2. The method according to claim 1, wherein the bioadhesive gel exhibits adhesive properties at or above 98 degrees Fahrenheit.

3. The method according to claim 1, wherein the bioadhesive gel further comprises an antimicrobial agent.

4. The method according to claim 3, wherein the antimicrobial is an inorganic ion releasing material.

5. The method according to claim 1, wherein the chitosan is at least 80% deacetylated.

6. The method according to claim 1, wherein the bioadhesive material comprises between 2.5% and 6% by weight of chitosan.

7. The method according to claim 6, wherein the bioadhesive material comprises between 1% and 7% by volume of lactic acid.

8. The method according to claim 1, wherein the bioadhesive material comprises a high molecular weight polysaccharide.

9. The method according to claim 1, wherein the bioadhesive material comprises an acidic solvent.

10. The method according to claim 9, wherein the acidic solvent is one of acetic acid and lactic acid.

11. The method according to claim 10, wherein the bioadhesive material comprises between 1% and 18% by volume of alcohol.

12. The method according to claim 1, wherein the bioadhesive material comprises glycerin.

13. The method according to claim 12, wherein the bioadhesive material comprises between 5% and 25% by volume of glycerin.

14. The method according to claim 1, wherein the bioadhesive material comprises one of aloe, vitamin E, Polyethylene Glycol (PEG), and Polyvinyl Alcohol (PVA).

15. The method according to claim 1, wherein the bioadhesive material comprises alcohol.

* * * * *